United States Patent [19]

Ife et al.

[11] Patent Number: 5,082,848

[45] Date of Patent: Jan. 21, 1992

[54] SUBSTITUTED 4-AMINOQUINOLINE DERIVATIVES AS GASTRIC ACID SECRETION INHIBITORS

[75] Inventors: Robert J. Ife, Stevenage; Thomas H. Brown, Tewin; Colin A. Leach, Stevenage, all of England

[73] Assignee: Smith Kline & French Laboratories, Ltd., Welwyn Garden City, England

[21] Appl. No.: 315,369

[22] Filed: Feb. 23, 1989

[30] Foreign Application Priority Data

Feb. 25, 1988 [GB] United Kingdom ............... 8804446

[51] Int. Cl.$^5$ .................... A61K 31/45; C07D 215/42
[52] U.S. Cl. .................... 514/313; 546/159; 546/160; 546/161; 546/162
[58] Field of Search ............... 546/159, 160, 161, 162; 514/313

[56] References Cited

U.S. PATENT DOCUMENTS

| | | | |
|---|---|---|---|
| 2,652,398 | 9/1953 | Kaye | 546/159 |
| 3,470,186 | 9/1969 | Hanifin et al. | 546/159 |
| 4,343,804 | 8/1982 | Munson, Jr. et al. | 546/159 |
| 4,806,549 | 2/1989 | Ife et al. | 546/159 |
| 4,806,550 | 2/1989 | Ife et al. | 546/159 |

FOREIGN PATENT DOCUMENTS

| | | | |
|---|---|---|---|
| 0259174 | 3/1988 | European Pat. Off. | 546/159 |
| 2106612 | 5/1972 | France | 546/159 |
| 2047244 | 11/1980 | United Kingdom | 546/159 |

*Primary Examiner*—Mukund J. Shah
*Assistant Examiner*—E. C. Ward
*Attorney, Agent, or Firm*—Dara L. Dinner; Stephen Venetianer; Edward T. Lentz

[57] ABSTRACT

Substituted 4-aminoquinoline derivatives of the formula:

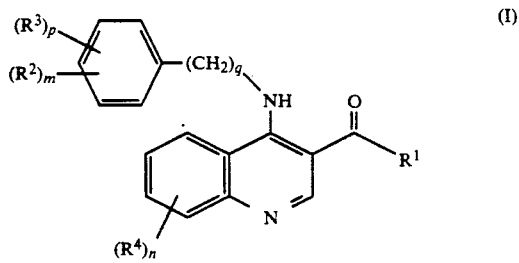

wherein $R^1$ is hydrogen, $C_{1-6}$ alkyl, $C_{1-6}$alkoxy$C_{1-6}$alkyl; $C_{3-6}$cycloalkyl, $C_{3-6}$cycloalkyl-$C_{1-6}$alkyl, phenyl $C_{1-6}$ alkyl, the phenyl groups being optionally substituted;

$R^2$ is hydroxy $C_{1-6}$alkyl, $C_{1-6}$ alkoxy$C_{1-6}$alkyl or two adjacent groups $R^2$ together form a $C_{1-4}$ alkylenedioxy group;

$R^3$ is hydrogen, $C_{1-6}$ alkyl, $C_{1-6}$ alkoxy, amino, $C_{1-6}$alkylthio, halogen, cyano, hydroxy, C1-6alkanoyl, or trifluromethyl;

$R^4$ is hydrogen, $C_{1-6}$ alkyl, phenyl, $C_{1-6}$ alkoxy, $C_{1-6}$alkylthio, $C_{1-6}$alkanoyl, amino, $C_{1-6}$alkylamino, di- $C_{1-6}$alkyl amino, halogen, or trifluromethyl;

n is 1 or 2;
q is 0 to 4;
m is 1, 2, or 3; and
p is 1, 2, 3, or 4 provided that m+p is not greater than 5;

or a salt thereof are useful as inhibitors of gastric acid secretion.

21 Claims, No Drawings

SUBSTITUTED 4-AMINOQUINOLINE DERIVATIVES AS GASTRIC ACID SECRETION INHIBITORS

The present invention relates to novel substituted quinoline derivatives, processes for their preparation, intermediates useful in their preparation, pharmaceutical compositions containing them and their use in therapy.

Substituted quinoline derivatives having activity as inhibitors of gastric acid secretion are known in the art. For example, U.S. Pat. No. 4,343,804 and EP 259174-A disclose series of 4-phenylaminoquinoline compounds in which the phenyl ring is optionally substituted by a range of substituents, for example, alkyl, alkylthio, alkoxy, halogen or cyano groups. The present invention relates to substituted quinoline derivatives in which the 4-phenylamino ring is substituted by a range of novel substituents, and which have been found to be potent inhibitors of gastric acid secretion.

Accordingly, the present invention provides, in a first aspect, a compound of structure (I):

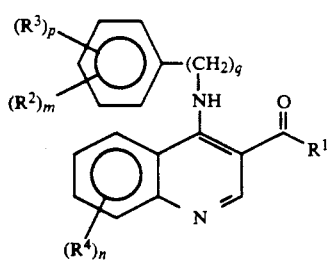

in which
$R^1$ is hydrogen, $C_{1-6}$alkyl, $C_{1-6}$alkoxy, $C_{1-6}$alkoxy$C_{1-6}$alkyl, $C_{3-6}$cycloalkyl, $C_{3-6}$cycloalkyl$C_{1-6}$alkyl, phenyl, phenyl$C_{1-6}$alkyl, the phenyl groups being optionally substituted;
$R^2$ is hydroxy$C_{1-6}$alkyl, $C_{1-6}$alkoxy$C_{1-6}$alkyl, or two adjacent groups $R^2$ together form a $C_{1-4}$alkylenedioxy group;
$R^3$ is hydrogen, $C_{1-6}$alkyl, $C_{1-6}$alkoxy, amino, $C_{1-6}$alkylthio, halogen, cyano, hydroxy, $C_{1-6}$alkanoyl or trifluoromethyl;
$R^4$ is hydrogen, $C_{1-6}$alkyl, phenyl, $C_{1-6}$alkoxy, $C_{1-6}$alkylthio, $C_{1-6}$alkanoyl, amino, $C_{1-6}$alkylamino, di-$C_{1-6}$alkylamino, halogen, trifluoromethyl or cyano;
n is 1 or 2;
q is 0 to 4;
m is 1, 2 or 3; and
p is 1, 2, 3, or 4 provided that m+p is not greater than 5; or a salt thereof.

Suitably, $R^1$ is hydrogen, $C_{1-6}$alkyl, $C_{1-6}$alkoxy, $C_{1-6}$alkoxyalkyl, $C_{3-6}$cycloalkyl, $C_{3-6}$cycloalkyl$C_{1-6}$alkyl, phenyl or phenyl$C_{1-6}$alkyl, the phenyl groups being optionally substituted. Preferably $R^1$ is hydrogen, $C_{1-6}$alkyl, $C_{1-6}$alkoxy or $C_{1-6}$alkoxyalkyl. More preferably $R^1$ is $C_{1-6}$alkyl or $C_{1-6}$alkoxy. Most preferably $R^1$ is $C_{1-6}$alkyl, in particular n-propyl.

Suitably m is 1 to 3 and $R^2$ is hydroxy$C_{1-6}$alkyl or $C_{1-6}$alkoxy$C_{1-6}$alkyl group or two groups $R^2$ together form a $C_{1-4}$alkylenedioxy group. Preferably, m is 2 and two groups $R^2$ together form a $C_{1-4}$alkylenedioxy group, in particular a methylenedioxy group.

Suitably $R^3$ is hydrogen, $C_{1-6}$alkyl, $C_{1-6}$alkoxy, amino, $C_{1-6}$alkylthio, halogen, cyano, hydroxy, carbamoyl, carboxy, $C_{1-6}$alkanoyl, trifluoromethyl or nitro.

Preferably $R^3$ is hydrogen, $C_{1-6}$alkyl or $C_{1-6}$alkoxy; most preferably $C_{1-6}$alkyl or $C_{1-6}$alkoxy.

Suitably p is 1 to 3; preferably p is 0 or 1, most preferably 1 and the group $R^3$ is in the 2-position of the phenyl ring.

Suitably, n is 1 or 2 and one group $R^4$ is in the 8-position. Preferably n is 1, and the group $R^4$ is in the 8-position of the quinoline ring.

Suitably $R^4$ is hydrogen, $C_{1-6}$alkyl, phenyl, $C_{1-6}$alkoxy, $C_{1-6}$alkylthio, $C_{1-4}$alkanoyl, amino, $C_{1-6}$alkylamino, di$C_{1-6}$alkylamino, halogen, trifluoromethyl or cyano. Preferably $R^4$ is hydrogen, $C_{1-6}$alkoxy, for example methoxy, or $C_{1-6}$alkyl, for example, methyl.

Suitably q is 0 to 4; preferably q is 1 to 4; most preferably q is 0.

$C_{1-6}$alkyl groups (either alone or as part of another group) can be straight or branched.

Phenyl $C_{1-6}$alkyl groups include for example benzyl, phenylethyl, phenylpropyl and phenylbutyl groups; and groups in which the alkyl portion is branched e.g. 1-methylbenzyl.

Substituted phenyl and phenyl $C_{1-6}$alkyl groups $R^1$ include, for example phenyl groups substituted by 1 to 3 substituents selected from $C_{1-6}$alkyl, $C_{1-6}$alkoxy, amino, $C_{1-6}$alkylthio, halogen, cyano, hydroxy, carbamoyl, carboxy, $C_{1-6}$alkanoyl, trifluoromethyl and cyano.

It will be appreciated that compounds of structure (I) in which one or more of $R^1$ to $R^4$ is a $C_{3-6}$alkyl group (either alone or as part of another group for example a benzyl or phenethyl group) may contain an asymmetric center due to the presence of the $C_{3-6}$alkyl group. Such compounds will exist as two (or more) optical isomers (enantiomers). Both the pure enantiomers, racemic mixtures (50% of each enantiomer) and unequal mixtures of the two are included within the scope of the present invention. Further, all diastereomeric forms possible (pure enantiomers and mixtures thereof) are within the scope of the invention.

Compounds of structure (I) can form salts with suitable acids and bases, in particular they can form pharmaceutically acceptable acid addition salts with suitable organic and inorganic acids the nature of which will be apparent to persons skilled in the art. For example, pharmaceutically acceptable salts can be formed by reaction with hydrochloric, sulphuric, or phosphoric acids; aliphatic, aromatic or heterocyclic sulphonic acids or carboxylic acids such as for example, citric, maleic or fumaric acids.

In a further aspect, the present invention provides a process for the preparation of a compound of structure (I) which comprises (a) reaction of a compound of structure (II) with a compound of structure (III):

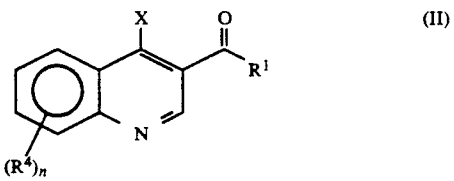

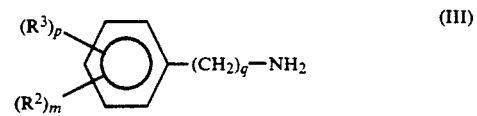

in which $R^1$, $R^2$, $R^3$, $R^4$, p, q, n and m are as described for structure (I) and X is a group displaceable by an amine;

(b) reduction of a compound of structure (IV)

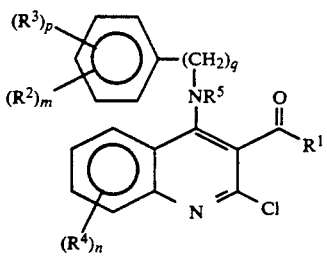

in which $R^1$, $R^2$, $R^3$, $R^4$, p, q, n and m are as described for structure (I); and $R^5$ is hydrogen or a nitrogen protecting group;

(c) for compounds of structure (I) in which $R^1$ is other than $C_{1-6}$alkoxy, oxidation of a compound of structure (V)

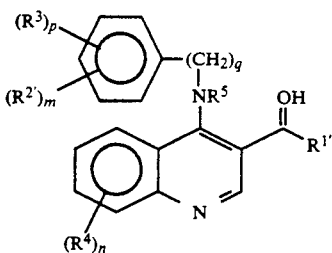

in which $R^3$, $R^4$, n, p, q and m are as described for structure (I), $R^{1'}$ is a group $R^1$ other than $C_{1-6}$alkoxy, $R^5$ is hydrogen or a nitrogen protecting group and $R^{2'}$ is an optionally protected group $R^2$; and thereafter if desired, removing any protecting groups;
converting a group $R^1$ into another group $R^1$;
forming a salt.

Suitable groups X displaceable by an amine, include for example, halo moieties, aryl or alkylsulphonates, for example, toluene-p-sulphonate or methane sulphonate, alkylthio, alkylsulphonyl, alkylsulphinyl, alkoxy or aryloxy groups. Preferably X is a halo moiety, for example, chloro or bromo, or an aryloxy group such as phenoxy.

Suitable nitrogen protecting groups $R^5$ and protected groups $R^2$ will be apparent to those skilled in the art for example as described in "Protective Groups in Organic Synthesis" T. W. Greene, 1981 (Wiley). In particular, protected groups $R^2$ are those in which the free hydroxy groups are protected, for example as acetoxy groups or benzoyloxy groups.

The reaction between compounds of structure (II) and compounds of structure (III) is carried out in an organic solvent at a temperature of between ambient and reflux temperature of the solvent used. Suitable solvents include, for example, tetrahydrofuran, dioxan or anisole. Preferably the reaction is carried out at reflux temperature in dioxan as a solvent.

The reduction of a compound of structure (IV) is carried out by for example hydrogenation, over a noble metal catalyst in a suitable solvent. Suitably the reaction is carried out over a palladium on carbon catalyst in ethanol as a solvent.

The compounds of structure (IV) can be prepared from the corresponding compounds of structure (VI)

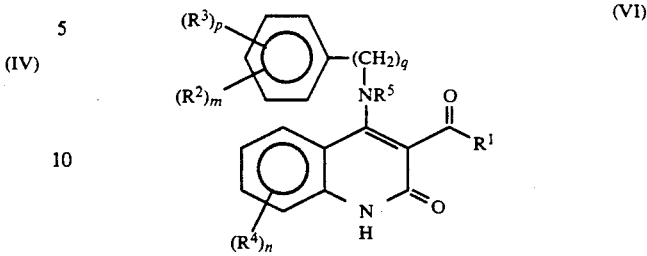

in which $R^1$, $R^2$, $R^3$, $R^4$, $R^5$, n, m, q and p are as hereinbefore described, by reaction with, for example, phosphorus oxychloride.

The oxidation of a compound of structure (V) is carried out in a suitable solvent in the presence of an oxidising agent. Suitable oxidising agents include, for example, manganese dioxide or chromium trioxide.

Suitable interconversions of groups $R^1$ will be apparent to those skilled in the art, for example compounds of structure (I) in which $R^1$ is $C_{2-6}$alkyl, $C_{3-6}$cycloalkyl$C_{2-6}$alkyl or optionally substituted phenyl$C_{1-6}$-alkyl can be prepared by alkylation of the following compounds of structure (IA) :

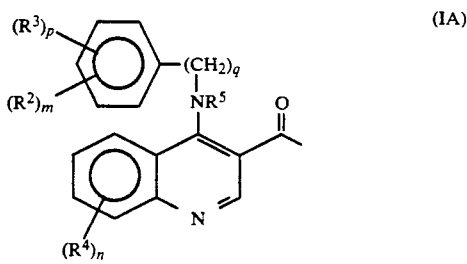

in which $R^2$, $R^3$, n, m and p are as described for structure (I) and $R^5$ and $R^6$ are as described for structure (IV).

The alkylation of compounds of structure (IA) is carried out in the presence of an alkylating agent in a suitable organic solvent at a temperature of between ambient and reflux temperature of the solvent used in the presence of a strong base. Suitable alkylating agents include, for example alkyl or aralkyl halides such as methyl or benzyl iodide and dialkyl sulphates such as dimethyl or diethylsulphate. Suitable strong bases include, for example, sodium hydride, lithium diisopropylamide or dimsyl sodium (the sodium salt of dimethyl sulphoxide). Subsequent removal of any protecting groups present affords the desired compounds of structure (I).

The intermediates of structure (II), (IV), (V) and (VI) can be prepared by standard techniques.

The intermediates of structure (III) are commercially available or can be prepared by standard techniques.

The compounds of structure (I) and their pharmaceutically acceptable salts exert an anti-secretory effect by inhibition of the gastrointestinal $H^+K^+$ATPase enzyme (Fellenius, E., Berglindh, T., Sachs, G., Olke, L., Elander, B., Sjostrand, S. E., and Wallmark, B., 1981, Nature, 290, 159-61).

In a further aspect therefore the present invention provides compounds of structure (I) and pharmaceutically acceptable salts thereof for use in therapy. The compounds of structure (I) and their pharmaceutically acceptable salts inhibit exogenously and endogenously stimulated gastric acid secretion and are useful in the treatment of gastrointestinal diseases in mammals, in particular humans. Such diseases include, for example, gastric and duodenal ulcers, aspiration pneumonitis and Zollinger-Ellison Syndrome.

Further, the compounds of structure (I) can be used in the treatment of other disorders where an anti-secretory effect is desirable for example in patients with gastritis, NSAID induced gastritis, acute upper intestinal bleeding, in patients with a history of chronic and excessive alcohol consumption, and in patients with gastro oesophageal reflux disease (GERD).

In therapeutic use, the compounds of the present invention are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The present invention also provides a method of inhibiting gastric acid secretion which comprises administering to a mammal in need thereof an effective amount of a compound of the formula (I) or a pharmaceutically acceptable salt thereof; and a method of treatment of diseases of the stomach or intestine based on increased acid secretion which comprises administering to a mammal in need thereof an effective amount of a compound of the formula (I) or a pharmaceutically acceptable salt thereof.

The pharmaceutically acceptable compounds of the invention will normally be administered to a subject for the treatment of gastro-intestinal diseases and other conditions caused or exacerbated by gastric acidity. The daily dosage regimen for an adult patient may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the formula (I) or a pharmaceutically acceptable salt thereof calculated as the free base, the compound being administered 1 to 4 times per day. Suitably the compounds will be administered for a period of continuous therapy, for example for a week or more.

In addition, the compounds of the present invention can be co-administered with further active ingredients, such as antacids (for example magnesium carbonate or hydroxide and aluminium hydroxide), non-steroidal anti-flammatory drugs (for example indomethacin, aspirin or naproxen), steroids, or nitrite scavengers (for example ascorbic acid or aminosulphonic acid), or other drugs used for treating gastric ulcers (for example pirenzipine, prostanoids for example 16, 16 dimethyl $PGE_2$, or histamine $H_2$-antagonists (for example, cimetidine).

The following examples illustrate the invention. Temperatures are recorded in degrees centigrade.

EXAMPLE 1

Preparation of 3-butyryl-4-(2-(hydroxymethyl)phenylamino)-8-methoxyquinoline

3-Butyryl-4-chloro-8-methoxyquinoline (2.64 g, 10 mmol) was dissolved in 1,4-dioxan (10 ml), 2-aminobenzyl alcohol (1.85 g, 15 mmol) added, and the mixture heated to reflux for 5 minutes. The dioxan was evaporated, water added, and the product extracted into dichloromethane. Chromatography (silica gel, ethyl acetate) and recrystallisation from ethyl acetate gave 3-butyryl-4-(2-(hydroxymethyl)phenylamino)-8-methoxyquinoline (1.86 g, 53%), m.p. 159°–161°.

$C_{21}H_{22}N_2O_3$: Found C 71.90, H 6.22, N 7.95; Requires C 71.98, H 6.33, N 7.99.

EXAMPLE 2

Preparation of 3-butyryl-4-(2-methoxymethylphenylamino)-8-methoxyquinoline

2-Methoxymethylaniline (1.0 g, 7.2 mmol) and 3-butyryl-4-chloro-8-methoxyquinoline (1.9 g, 7.2 mmol) were heated together under reflux in 1,4-dioxan (50 ml) for 2 hours. The solvent was evaporated and the residue dissolved in dichloromethane, washed with water, sodium hydrogen carbonate solution and brine, dried and evaporated. Recrystallisation from ethanol-water afforded 3-butyryl-4-(2-methoxymethyl-phenylamino)-8-methoxyquinoline, m.p. 128°–30°.

$C_{22}H_{24}N_2O_3 \cdot 0.2H_2O$; Found C 71.78, H 6.55, N 7.60; Requires C 71.79, H 6.68, N 7.61.

EXAMPLE 3

Preparation of 3-butyryl-4-(3,4-(methylenedioxy)phenylamino)-8-methoxyquinoline 3,4-(Methylenedioxy)aniline (1.0 g, 7.3 mmol) and 3-butyryl-4-chloro-8-methoxyquinoline (1.4 g, 5.3 mmol) were stirred at room temperature in tetrahydrofuran (20 ml) for 1 hour. The solvent was evaporated and the residue chromatographed (silica gel-dichloromethane to 1% methanol in dichloromethane). Evaporation of the required fractions and crystallisation from ether afforded 3-butyryl-4-(3,4-(methylenedioxy)phenylamino)-8-methoxyquinoline as yellow crystals, m.p. 145°–7°.

$C_{21}H_{20}N_2O_4$: Found C 69.26, H 5.53, N 7.62; Requires C 69.22, H 5.53, N 7.69.

EXAMPLE 4

Preparation of 3-butyryl-4-(4-hydroxymethylphenylamino)-8-methoxyquinoline

3-Butyryl-4-chloro-8-methoxyquinoline (2 g, 8 mmol), 4-aminobenzyl alcohol (2.3 g, 12 mmol) and 1,4-dioxan (50 ml) were heated at 70° for 1.5 hours, then more amine (0.9 g, 8 mmol) was added and heating continued for a further 6 hours. The solvent was evaporated and the product converted to free base. Recrystallisation from chloroform/ether gave 3-butyryl-4-(4-hydroxymethylphenylamino)-8-methoxyquinoline (1.5 g), m.p. 187°–189°.

$C_{21}H_{22}N_2O_3$: Found C 71.82, H 6.30, N 7.95; Requires C 71.98, H 6.33, N 7.99.

EXAMPLE 5

Preparation of 3-butyryl-4-(3,4-methylenedioxy-2,6-dimethylphenylaminio)-8-methoxyquinoline A. Preparation of 3,5-dimethyl-1,2-(methylenedioxy)benzene 3,5-Dimethylcatechol (13.8 g) in a vigorously stirred mixture of dimethylsulphoxide (150 ml), dichloromethane (10 g) and sodium hydroxide (8.3 g) under nitrogen atmosphere was heated over an oil bath (120°–130° C.) for 2 hours. The mixture was poured into water (600 ml) and extracted (×4) with ether. The ethereal solution was dried and evaporated to afford 3,5-dimethyl-1,2-(methylenedioxy)benzene (14.0 g, 93%) as an oil.

B. Preparation of 3,5-dimethyl-4-nitro-1,2-(methylenedioxy)benzene

Finely ground cupric nitrate (12.1 g) was stirred in acetic anhydride (150 ml) at 10° C. and 3,5-dimethyl-1,2-(methylenedioxy)benzene (7.5 g) in acetic anhydride (50 ml) was added dropwise. The mixture was stirred for 1 hour then water (150 ml) was added, keeping the temperature to around 10° C. and left to stand at room temperature overnight. The mixture was cooled to 0° C. by the addition of ice and the solid 3,5-dimethyl-4-nitro-1,2-(methylenedioxy)benzene (8.0 g, 82%) was filtered off, washed with ice-water and dried, m.p. 75°–6° C.

C. Preparation of 2,6-dimethyl-3,4-(methylenedioxy)aniline 3,5-Dimethyl-4-nitro-1,2-(methylenedioxy)benzene (5.0 g) and 10% palladium on charcoal catalyst (1.2 g) in ethanol (250 ml) was shaken in a hydrogen atmosphere (50 p.s.i.) at 40° C. for 4 hours. The mixture was filtered through celite and evaporated to leave 2,6-dimethyl-3,4-(methylenedioxy)aniline (2.8 g, 68%) as a dark oil.

D. Preparation of 3-butyryl-4-)3,4-methylenedioxy-2,6-dimethylphenylamino)-8-methoxyquinoline 2,6-Dimethyl-3,4-(methylenedioxy)aniline (1.67 g, 20 mmol) and 3-butyryl-4-chloro-8-methoxyquinoline (2.3 g, 10 mmol) were heated together under reflux in 1,4-dioxan (50 ml) for 2 hours. The solvent was evaporated and the residue was dissolved in dichloromethane, washed with 2M HCl, sodium hydrogen carbonate solution (×2) and brine. The organic solution was dried, filtered and evaporated to a solid which was recrystallized from ethanol to give 3-butyryl-4-(3,4-methylenedioxy-2,6-dimethylphenylamino)-8-methoxyquinoline (17 g, 43%), m.p. 150°–2° C.

$C_{23}H_{24}N_2O_4 \cdot 0.1H_2O$: Found C 69.63, H 5.92, N 7.01; Requires C 69.65, H 6.22, H 7.06.

EXAMPLE 6

Preparation of 3-butyryl-4-(3-hydroxymethyl-2-methylphenylamino)-8-methoxyquinoline A. Preparation of 3-amino-2-methylbenzyl alcohol A solution of 2-methyl-3-nitrobenzyl alcohol (2.0 g, 12 mmol) in ethanol (100 ml) was hydrogenated over 10% palladium/charcoal (0.1 g) for 2 hours, at an initial pressure of 3.5 bar. The solution was filtered through celite and evaporated to give 3-amino-2-methylbenzyl alcohol (1.67 g, quantitative), m.p. 104°–106°

B. Preparation of 3-butyryl-4-(3-hydroxymethyl-2-methylphenylamino)-8-methoxyquinoline A solution of 3-butyryl-4-chloro-8-methoxyquinoline (1.32 g, 5 mmol) and 3-amino-2-methylbenzyl alcohol (0.82 g, 6 mmol) in dioxan (25 ml) was heated at reflux for 1.5 hours, then the solvent evaporated. Aqueous sodium bicarbonate was added, the product extracted into dichloromethane, dried and evaporated. Recrystallisation from methanol gave 3-butyryl-4-(3-hydroxymethyl-2-methylphenylamino)-8-methoxyquinoline (1.20 g, 66%), m.p. 186°–188°.

$C_{22}H_{24}N_2O_3$: Found C 72.66, H 6.66, N 7.66; Requires C 72.50, H 6.64, N 7.69.

EXAMPLE 7

Preparation of 3-butyryl-4-(5-hydroxymethyl-2-methylphenylamino)-8-methoxyquinoline A. Preparation of 3-amino-4-methylbenzyl alcohol Methyl 3-amino-4-methylbenzoate (16.52 g, 0.1 mol) was dissolved in diglyme (150 ml), lithium borohydride (2.18 g, 0.1 mol) added, and the solution stirred at room temperature overnight. A further portion of lithium borohydride (2.18 g, 0.1 mol) was added, and the mixture heated at reflux for 20 minutes. The reaction was quenched with water, the solvent evaporated, the residue dissolved in water, the solution adjusted to pH 5 with hydrochloric acid, and the product extracted into dichloromethane. Drying, evaporation and trituration with ether gave 3-amino-4-methylbenzyl alcohol (7.3 g, 54%), m.p. 105°–107°.

B. Preparation of 3-butyryl-4-(5-hydroxymethyl-2-methylphenylamino)-8-methoxyquinoline A solution of 3-butyryl-4-chloro-8-methoxyquinoline (0.80 g, 3 mmol) and 3-amino-4-methylbenzyl alcohol (0.48 g, 3.5 mmol) in dioxan (10 ml) was heated at reflux for 1.5 hours, then the solvent evaporated. Aqueous sodium bicarbonate was added, the product extracted into dichloromethane, dried and evaporated. Recrystallisation from methanol gave 3-butyryl-4-(5-hydroxymethyl-2-methylphenylamino)-8-methoxyquinoline (0.65 g, 59%) 180°–181°.

$C_{22}H_{24}N_2O_3$: Found C 72.61, H 6.57, N 7.72; Requires C 72.50, H 6.64, N 7.69.

EXAMPLE A

A tablet for oral administration is prepared by combining

|  | Mg/Tablet |
|---|---|
| Compound of structure (I) | 100 |
| lactose | 153 |
| Starch | 33 |
| crospovidone | 12 |
| microcrystalline cellulose | 30 |
| magnesium stearate | 2 |
|  | 330 mg | into a 9 mm tablet.

EXAMPLE B

An injection for parenteral administration is prepared from the following

|  | % w:w |
|---|---|
| Compound of Example 3 | 0.50% (w:v) |
| 1M citric acid | 30% (v:v) |
| sodium hydroxide (qs) | to pH 3.2 |
| water for injection EP | to 100 ml |

The compound of Example 3 is dissolved in the citric acid and the pH slowly adjusted to pH 3.2 with the sodium hydroxide solution. The solution is then made up to 100 ml with water, sterilised by filtration and sealed into appropriately sized ampoules and vials.

Biological Data

A. $H^+K^+ATPase$ Activity

The effects of a single high concentration (100 μM) of a compound of structure (I) on $K^+$-stimulated ATPase activity in lyophilised gastric vesicles was determined. Preferred compounds of structure (I) were also tested over a range of concentrations to determine $IC_{50}$ values.

(i) Preparation of lyophilised gastric vesicles (H/K-ATPase)

Lyophilised gastric vesicles were prepared from pig fundic mucosa after the method of Keeling et. al. (Biochem. Pharmacol., 34, 2967, 1985).

(ii) $K^+$-stimulated ATPase activity $K^+$-stimulated ATPase activity was determined at 37° C. in the presence of the following: 10 mM Pipes/Tris buffer pH 7.0, 2 mM $MgSO_4$, 1 mM KCl, 2 mM $Na_2ATP$ and 3-6 μg protein/ml lyophilised gastric vesicles. After incubation for 30 minutes, the inorganic phosphate hydrolysed from ATP was determined by the method of Yoda and Hokin (Biochem. Biophys. Res. Commun. 40, 880, 1970).

Compounds of structure (I) were dissolved in dimethylsulphoxide which up to the highest concentration used had no effect on $K^+$-stimulated ATPase activity.

The effect of the highest concentration of each compound of structure (I) on the recovery of a standard amount of inorganic phosphate was also determined.

The $IC_{50}$ values (μM) were as follows:

| Compound | $IC_{50}$ (μM) |
|---|---|
| 1 | 12 |
| 2 | 5.5 |
| 3 | 3.6 |
| 4 | 38% @ 100 μM |
| 5 | 2.7 |
| 6 | 6.0 |
| 7 | 10.2 |

B. Rat Lumen Perfused Stomach (pentagastrin stimulated gastric acid secretion).

Using a modification of the procedure described by Ghosh & Schild (Br. J. Pharmacology, 13, 54, 1958), the compounds of the following examples were found on i.v. administration at a concentration of 10 μmole/kg to cause an inhibition of pentagastrin stimulated gastric acid secretion as follows:

| Example No. | % inhibition |
|---|---|
| 1 | 33 |
| 2 | 43 |
| 3 | 20 |
| 4 | 51 |
| 5 | 44 |
| 7 | 25 |

What is claimed is:

1. A compound of the structure (I):

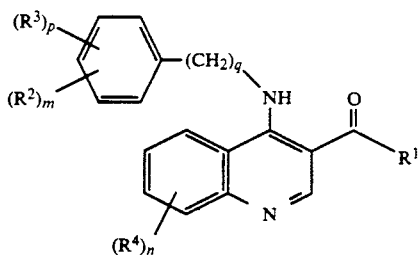

wherein $R^1$ is hydrogen, $C_{1-6}$alkyl, $C_{1-6}$alkoxy$C_{1-6}$alkyl, $C_{3-6}$cycloalkyl, $C_{3-6}$cycloalkyl-$C_{1-6}$alkyl, phenyl, phenyl $C_{1-6}$alkyl, the phenyl groups being optionally substituted by 1 to 3 substituents selected from $C_{1-6}$alkyl, $C_{1-6}$alkoxy, amino, $C_{1-6}$alkylthio, halogen, hydroxy, carbamoyl, carboxy, $C_{1-6}$alkanoyl, trifluoromethyl or cyano;

$R^2$ is hydroxy$C_{1-6}$alkyl, $C_{1-6}$alkoxy$C_{1-6}$alkyl or two adjacent $R^2$ groups together form a $C_{1-4}$alkylenedioxy group;

$R^3$ is hydrogen, $C_{1-6}$alkyl, $C_{1-6}$alkoxy, amino, $C_{1-6}$alkylthio, halogen, cyano, hydroxy, C1-6alkanoyl, or trifluoromethyl;

$R^4$ is hydrogen, $C_{1-6}$alkyl, phenyl, $C_{1-6}$alkoxy, $C_{1-6}$alkylthio, $C_{1-6}$alkanoyl, amino, $C_{1-6}$alkylamino, di-$C_{1-6}$alkyl amino, halogen, or trifluromethyl;

n is 1 or 2;

q is 0 or 4;

m is 1, 2, or 3; and p is 1, 2, 3, or 4 provided that m+p is not greater than 5;
or a salt thereof.

2. A compound according to claim 1 in which m is 1 and $R^2$ is in the 2-position of the phenyl ring.

3. A compound according to claim 1 or 2 in which the group $R^4$ is a $C_{1-6}$alkyl or $C_{1-6}$alkoxy group in the 8-position of the quinoline ring.

4. A compound according to claim 1 which is 3-butyryl-4-(2-(hydroxymethyl)phenylamino)-8-methoxyquinoline.

5. A compound according to claim 1 which is 3-butyryl-4-(2-methoxymethylphenylamino)-8-methoxyquinoline.

6. A compound according to claim 1 which is 3-butyryl-4-(3,4-(methylenedioxy)phenyl-amino)-8-methoxyquinoline.

7. A compound according to claim 1 which is 3-butyryl-4-(4-hydroxymethylphenylamino)-8-methoxyquinoline.

8. A compound according to claim I which is 3-butyryl-4-(3,4-methylenedioxy-2,6-dimethylphenylamino)8-methoxyquinoline.

9. A compound according to claim 1 which is 3-butyryl-4-(3-hydroxymethyl-2-methylphenylamino)-8-methoxyquinoline.

10. A compound according to claim 1 which is 3-butyryl-4-(5-hydroxymethyl-2-methylphenylamino)-8-methoxyquinoline.

11. A pharmaceutical composition comprising a compound according to claim I or a pharmaceutically acceptable salt thereof and a pharmaceutically acceptable carrier.

12. A method of inhibiting gastric acid secretion which comprises administering to a mammal in need thereof an effective amount of a compound according to claim I.

13. A method of treatment of gastrointestinal diseases and other conditions caused or exacerbated by gastric acidity which comprises administering to a mammal in need thereof an effective amount of a compound according to claim 1.

14. A compound of structure (IV)

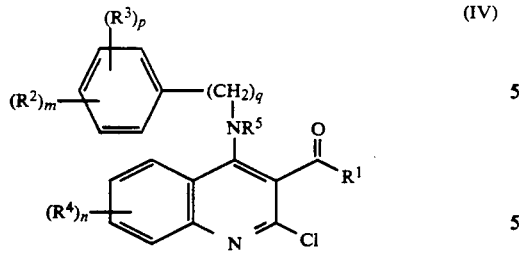

wherein
$R^1$ is hydrogen, $C_{1-6}$alkyl, $C_{1-6}$alkoxy$C_{1-6}$alkyl, $C_{3-6}$cycloalkyl, $C_{1-6}$cycloalkyl-$C_{1-6}$alkyl, phenyl, phenyl$C_{1-6}$alkyl, the phenyl groups being optionally substituted by 1 to 3 substituents selected from $C_{1-6}$alkyl, $C_{1-6}$alkoxy, amino, $C_{1-6}$alkylthio, halogen, hydroxy, carbamoyl, carboxy, $C_{1-6}$alkanoyl, trifluromethyl or cyano;

$R^2$ is hydroxy$C_{1-6}$alkyl, $C_{1-6}$alkoxy$C_{1-6}$alkyl, or two adjacent groups $R^2$ together form a $C_{1-4}$alkylenedioxy group;

$R^3$ is hydrogen, $C_{1-6}$alkyl, $C_{1-6}$alkoxy, amino, $C_{1-6}$alkylthio, halogen, cyano, hydroxy, $C_{1-6}$alkanoyl, or trifluoromethyl;

$R^4$ is hydrogen, $C_{1-6}$alkyl, phenyl, $C_{1-6}$alkoxy, $C_{1-6}$alkylthio, $C_{1-6}$alkanoyl, amino, $C_{1-6}$alkylamino, di-$C_{1-6}$alkylamino, halogen, or trifluromethyl;

n is 1 or 2;
q is 0 to 4;
m is 1, 2, or 3;
p is 1, 2, 3 or 4 provided that m+p is not greater than 5; and $R^5$ is hydrogen or a nitrogen protecting group.

15. A compound of structure (V)

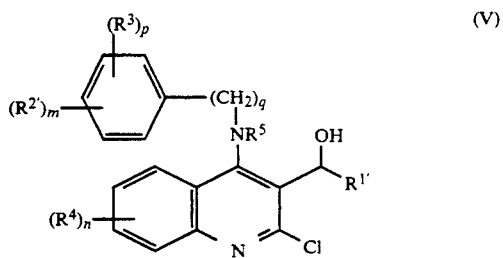

wherein
$R^{1'}$ is hydrogen, $C_{1-6}$alkyl, $C_{1-6}$alkoxy$C_{1-6}$alkyl, $C_{3-6}$cycloalkyl, $C_{1-6}$cycloalkyl-$C_{1-6}$alkyl, phenyl, phenyl$C_{1-6}$alkyl, the phenyl groups being optionally substituted to 1 to 3 substituents selected from $C_{1-6}$alkyl, $C_{1-6}$ alkoxy, amino, $C_{1-6}$alkylthio, halogen, cyano, hydroxy, carbamoyl, carboxy, $C_{1-6}$ alkanoyl, trifluoromethyl or:

$R^3$ is hydrogen, $C_{1-6}$alkyl, $C_{1-6}$alkoxy, amino, $C_{1-6}$alkylthio, halogen, cyano, hydroxy, $C_{1-6}$alkanoyl, or trifluoromethyl:

$R^4$ is hydrogen, $C_{1-6}$alkyl, phenyl, $C_{1-6}$alkoxy, $C_{1-6}$alkylthio, $C_{1-6}$alkanoyl, amino, $C_{1-6}$alkylamino, di-$C_{1-6}$alkylamino, halogen, or trifluoromethyl:

n is 1 or 2;
q is 0 to 4;
m is 1, 2, or 3;
p is 1, 2, 3 or 4 provided that m+p is not greater than 5;
$R^5$ is hydrogen or a nitrogen protecting group;
$R^{2'}$ is an optionally protected group $R^2$; and
$R^2$ is hydroxy$C_{1-6}$alkyl, $C_{1-6}$alkoxy$C_{1-6}$alkyl, or two adjacent groups $R^2$ together form a $C_{1-4}$alkylenedioxy group;

16. The compound according to claim 1 wherein q is 0.

17. The compound according to claim 16 wherein $R^2$ is hydroxy $C_{1-6}$alkyl.

18. The compound according to claim 16 wherein $R^2$ is $C_{1-6}$alkoxy $C_{1-6}$alkyl.

19. The compound according to claim 16 wherein $R^2$ is $C_{1-4}$alkylenedioxy.

20. The compound according to claim 17 wherein $R^2$ is hydroxymethyl.

21. The compound according to claim 17 wherein $R^2$ is methoxymethyl.

* * * * *